United States Patent
Radojicic

(10) Patent No.: US 8,096,967 B2
(45) Date of Patent: Jan. 17, 2012

(54) TISSUE ENGINEERED CEREBROSPINAL FLUID SHUNT

(76) Inventor: Milan Radojicic, Altadena, CA (US)

( * ) Notice: Subject to any disclaimer, the term of this patent is extended or adjusted under 35 U.S.C. 154(b) by 698 days.

(21) Appl. No.: 11/669,958

(22) Filed: Feb. 1, 2007

(65) Prior Publication Data

US 2007/0179427 A1 Aug. 2, 2007

Related U.S. Application Data

(60) Provisional application No. 60/766,634, filed on Feb. 2, 2006.

(51) Int. Cl.
*A61M 5/00* (2006.01)
(52) U.S. Cl. ................................. 604/9; 604/8
(58) Field of Classification Search .............. 604/6.16, 604/7–10, 266, 891.1; 424/422–426, 93.7, 424/484; 623/1.4, 1.42, 1.43, 1.46, 1.49, 623/1.16, 1.36, 9
See application file for complete search history.

(56) References Cited

U.S. PATENT DOCUMENTS

| | | | |
|---|---|---|---|
| 3,829,903 A | 8/1974 | Stati | |
| 5,686,289 A | 11/1997 | Humes | |
| 6,348,042 B1 * | 2/2002 | Warren, Jr. | 604/8 |
| 6,579,313 B2 * | 6/2003 | Dzau et al. | 623/1.4 |
| 7,049,057 B2 | 5/2006 | Atala | |
| 2006/0069425 A1 * | 3/2006 | Hillis et al. | 623/1.16 |
| 2007/0082393 A1 * | 4/2007 | Lodhi et al. | 435/325 |

OTHER PUBLICATIONS

Ziegelaar et al. "The characterisation of human respiratory epithelial cells cultured on resorbable scaffolds:first steps towards a tissue engineered tracheal replacement." 2002. Biomaterials. vol. 23. pp. 1425-1438.*

Radojicic, Milan. (Feb. 1, 2007) The Bioshunt. Retrieved Mar. 28, 2007 from http://www.deomedicus.com/education/the-bioshunt.html.

Baizabal, J.-M., et al., Neural Stem Cells in Development and Regenerative Medicine, Arch. Med. Res 34, 2003, pp. 572-588.

Cornford, E., et al., Localization of Brain Endothelial Luminal and Abluminal Transporters with Immunogold Electron Microscopy, NeuroRx: The Journal of the American Society for Experimental NeuroTherapeutics, vol. 2, Jan. 2005, pp. 27-43.

Duval, J.-L., et al., Use of the organotypic culture method to investigate drug-loaded CSF shunt, Journal of Controlled Release 116, 2006, pp. e50-e53.

Gabrion, J.B., et al., Ependymal and Choroidal Cells in Culture: Characterization and Functional Differentiation, Microscopy Research and Technique 41, 1998, pp. 124-157.

Junqueira Histology of Epithelium from Access Medicine (www.accessmedicine.com), 24 pages.

Koizumi, J., et al. Changes of Gap and Tight Junctions during Differentiation of Human Nasal Epithelial Cells Using Primary Human Nasal Epithelial Cells and Primary Human Nasal Fibroblast Cells in a Noncontact Coculture System, J Membrane Biol 218, 2007, pp. 1-7.

Seminatore, C., et al., The Postischemic Environment Differentially Impacts Teratoma or Tumor Formation After Transplantation of Human Embryonic Stem Cell-Derived Neural Progenitors, Stroke 41, 2010, pp. 153-159.

* cited by examiner

*Primary Examiner* — Leslie Deak
*Assistant Examiner* — Philip R Wiest
(74) *Attorney, Agent, or Firm* — Kang Lim

(57) ABSTRACT

This invention relates to cerebrospinal fluid shunts, and a method of treating shunt catheters, whereby the interior lumen of a shunt catheter, comprised of a biocompatible matrix, is seeded with cells for placement within cerebrospinal fluid pathways of the central nervous system. The seeded cells have at least one of the following characteristics: (1) they are of a polarized ependymal epithelial phenotype with tight junctional complexes and apical cilia directed toward the lumen of the catheter; (2) they maintain stem/progenitor characteristics and are capable of neurogenesis; (3) they maintain stem/progenitor characteristics and are capable of gliogenesis.

8 Claims, No Drawings

TISSUE ENGINEERED CEREBROSPINAL FLUID SHUNT

CROSS-REFERENCE TO RELATED APPLICATIONS

This application claims the benefit of provisional patent application Ser. No. 60/766,634, filed Feb. 2, 2006 by the present inventor.

FEDERALLY SPONSORED RESEARCH

Not applicable.

SEQUENCE LISTING OR PROGRAM

Not applicable.

BACKGROUND OF THE INVENTION

1. Field of the Invention

The field of the present invention is tissue engineering. In particular, this invention relates to cerebrospinal fluid shunts, specifically to an improved mechanism of cerebrospinal fluid diversion and central nervous system wound repair.

2. Prior Art

The diversion of cerebrospinal fluid from one location to another where it may be disposed is a well-known clinical strategy for a number of brain and spinal disorders, in fact comprising one of the most common neurosurgical procedures.

Prior art in shunt technology has emphasized the passive drainage of fluid across a pressure gradient regulated by valve mechanisms. However, this approach is subject to a number of potential failures. In addition to shunt infections, shunt failures may result from blockage of the proximal and/or distal catheters due to tissue ingrowth, cellular debris and clot. Valve malfunctions are possible, as well. These frequent failures result in undue patient morbidity and mortality.

Preventing shunt failures due to blockages have relied on mechanical (see Stati et. al., U.S. Pat. No. 3,829,903) or enzymatic means (see Warren, U.S. Pat. No. 6,348,042). However, no single strategy has emerged as a long-term, efficient and cost-effective solution.

It is an object of the present invention to provide a cerebrospinal fluid shunt that obviates or mitigates at least one of the disadvantages of the prior art, as well as providing advantages over that prior art.

The field of tissue engineering aims to combine mechanical and biological phenomenons into useful devices. Applications of tissue engineering have appeared in other organ systems, including the cardiovascular system (see Dzau et. al., U.S. Pat. No. 6,579,313), the renal system (see Humes et. al., U.S. Pat. No. 5,686,289) and the genitourinary system (see Atala et. al., U.S. Pat. No. 7,049,057). However, until this Applicant's invention, no such method or device has been applied to cerebrospinal fluid diversion. This device is a tissue engineered cerebrospinal fluid shunt with intraluminal seeded cells.

It is an object of this invention to provide new and additional auxiliary means for intraluminal fluid propulsion, namely the introduction of ciliated cellular elements. It is also an object of this invention to regulate the tonicity and translocation of intraluminal fluid by inherent cellular mechanisms. Furthermore, it is an object of this invention to prevent blockages of the shunt lumen through inherent enzymatic processes of the intraluminal matrix cells. Finally, recent attention has turned to the role of the cerebrospinal fluid flow and stem cell behavior. It is an object of this invention to seed stem/progenitor cells along the intraluminal matrix to provide for local and remote brain and spinal cord repair. This further results in a new system with improved properties over prior art systems. Other objects will be readily apparent based on the following detailed description.

DETAILED DESCRIPTION OF THE INVENTION

The present invention relates to a biocompatible shunt for the diversion of cerebrospinal fluid in which the luminal surface is seeded with at least one population of cells. In a preferred embodiment, the outer layer of cells is comprised of a polarized ependymal epithelial phenotype with tight junctional complexes and apical cilia directed toward the lumen of the catheter, whereas an inner layer of cells is comprised of stem/progenitor cell capable of glio- and neurogenesis. The cells are impregnated on a matrix coating the luminal surface of the shunt.

Characteristics of the outer cells suitable for the present invention, include (1.) apical cilia whose rhythmic beating (i.) promotes cerebrospinal fluid flow within the lumen of the catheter and (ii.) prevents obstruction of the catheter by tissue, clot and debris; (2.) tight junctions that prevent translocation of intraluminal fluid; (3.) cellular mechanisms to regulate the tonicity of intraluminal fluid through selective ion and protein exchange; (4.) cellular mechanisms for the spontaneous and continuous production, storage and release of enzymes that assist in the degradation of intraluminal tissue, clot and debris thereby maintaining patency of the shunt.

An additional characteristic of the present invention is the incorporation of an inner layer of cells with stem/progenitor characteristics. Cells have a finite life and most cell populations require regular turnover. The incorporation of a layer of stem/progenitor cells would allow for local repair of denuded shunt epithelium, thereby extending the life of the shunt. Furthermore, an additional characteristic of the present invention may allow for the differentiation, proliferation and migration of glial and neural precursors from the shunt intraluminal matrix into surrounding neural tissue for the purposes of therapeutic cell delivery and wound repair.

While the above description contains many specificities, these should not be construed as limitations on the scope of the invention, but as exemplifications of the presently preferred embodiments thereof. Many other ramifications and variations are possible within the teaching of the invention. For example, the shunt catheter may have other shapes suited for a particular cerebrospinal fluid pathway. Additionally, any ramification and variation of the cellular types described above are possible.

Thus the scope of the invention should be determined by the appended claims and their legal equivalents, rather than the examples given.

What is claimed:

1. A shunt, comprising:
   a biocompatible material configured to be implanted in a cerebrospinal fluid pathway and implantable in a cerebrospinal fluid pathway of the brain and spinal cord for the diversion of cerebrospinal fluid flow;
   a surface coating applied to an interior lumen surface of the shunt, said surface comprising a biocompatible matrix; and
   at least one population of cells impregnated in said coating, wherein at least one population of cells comprises ciliated tissue, whereby at least one population of cells has begun cellular differentiation, and wherein the at least one population of cells includes a luminal layer of cells and an abluminal layer of cells that is distinct from the luminal layer of cells in that the abluminal layer of cells is multipotent.

2. The shunt of claim 1, wherein the luminal layer of cells are a polarized ependymal epithelial phenotype with tight junctional complexes and apical cilia directed toward the lumen of the cerebrospinal fluid pathway.

3. The shunt of claim 1, wherein the abluminal layer of cells have stem/progenitor characteristics and are capable of neurogenesis.

4. The shunt of claim 1, wherein the abluminal layer of cells have stem/progenitor characteristics and are capable of gliogenesis.

5. The shunt of claim 1, wherein the biocompatible matrix comprises a polymer.

6. The shunt of claim 1, wherein the biocompatible matrix is seeded with the at least one additional cell population.

7. A tissue engineered cerebrospinal fluid shunt, comprising:
   a biocompatible material configured to be implanted in a cerebrospinal fluid pathway and implantable in a cerebrospinal fluid pathway of the brain and spinal cord for the diversion of cerebrospinal fluid flow;
   a surface coating applied to the interior lumen surface of the shunt, said surface comprising a biocompatible matrix;
   at least one luminal layer population of cells impregnated in said coating, wherein said luminal layer population of cells include ciliated tissue, and are of a polarized ependymal epithelial phenotype with tight junctional complexes and apical cilia directed toward the lumen of the cerebrospinal fluid pathway;
   a luminal surface seeded with intraluminal matrix cells having inherent enzymatic processes; and
   an abluminal layer of cells comprised of stem/progenitor cells having gliogenic and neurogenic properties.

8. The shunt of claim 7, wherein the biocompatible matrix comprises a polymer.

\* \* \* \* \*